United States Patent
Phillips

[11] Patent Number: 5,928,662
[45] Date of Patent: Jul. 27, 1999

[54] OCULAR DRUG DELIVERY DEVICE

[76] Inventor: Andrew F. Phillips, 1900 E. Ocean Blvd. #608, Long Beach, Calif. 90802

[21] Appl. No.: 08/900,806

[22] Filed: Jul. 25, 1997

Related U.S. Application Data

[60] Provisional application No. 60/022,841, Jul. 31, 1996.

[51] Int. Cl.$^6$ .............................. A61F 2/14; A61K 31/74
[52] U.S. Cl. ...................................... 424/427; 424/78.04
[58] Field of Search ................................. 424/427, 78.04

[56] References Cited

U.S. PATENT DOCUMENTS

| | | | |
|---|---|---|---|
| 3,075,527 | 1/1963 | Bechtold | 128/260 |
| 3,618,604 | 11/1971 | Ness | 128/260 |
| 3,818,909 | 6/1974 | Bratton | 128/232 |
| 3,916,899 | 11/1975 | Theeuwes et al. | 128/260 |
| 4,014,335 | 3/1977 | Arnold | 128/260 |
| 4,193,401 | 3/1980 | Marinello | 128/260 |
| 4,913,682 | 4/1990 | Shabo | 604/1 |
| 5,224,957 | 7/1993 | Gasser et al. | 623/6 |
| 5,314,419 | 5/1994 | Pelling | 604/294 |
| 5,368,582 | 11/1994 | Bertera | 604/295 |
| 5,378,475 | 1/1995 | Smith et al. | 424/473 |
| 5,382,243 | 1/1995 | Mulholland | 604/301 |
| 5,389,066 | 2/1995 | Rhame, Jr. | 602/74 |
| 5,472,436 | 12/1995 | Fremstad | 604/294 |

FOREIGN PATENT DOCUMENTS

| | | | |
|---|---|---|---|
| 1529143 | 10/1978 | United Kingdom | 604/294 |

*Primary Examiner*—Carlos A. Azpuru
*Attorney, Agent, or Firm*—David P. Gordon; David S. Jacobson; Thomas A. Gallagher

[57] ABSTRACT

An ocular drug delivery device includes a reservoir which holds medicine and is locatable outside the eye during drug delivery to a patient, and a conduit having one end coupled to the reservoir and a free end which is positionable within the fornix of the eye of a patient. Through gravity and/or capillary action, the medicine flows from the reservoir through the conduit and into the eye. The rate of delivery of the medicine to the eye may be adjusted according to the size and material of the conduit. According to a first embodiment, the reservoir is preferably made of an absorbent material and is provided with an impermeable backing which acts as a barrier between the medicine and facial skin of the patient. Preferably the backing has an edge to prevent medicine from rolling off the reservoir surface. The backing may also be provided with an adhesive for removably coupling the reservoir to the facial skin of the patient, particularly to an area adjacent the eye. According to a second embodiment, the reservoir is a hollow container and the conduit is a relatively narrow strip of an absorbent material running through a flexible tube. The reservoir is provided with an aperture through which medicine is provided to the reservoir, and preferably also includes an openable closure for alternately sealing the aperture and providing access to the reservoir.

20 Claims, 3 Drawing Sheets

OCULAR DRUG DELIVERY DEVICE

This application claims the benefit of Provisional Application Ser. No. 60/022,841, filed Jul. 31, 1996, entitled "Method and Apparatus for Improved Application of Topical Ocular Medicines Using a Novel Drop Reservoir to Achieve Higher and More Constant Levels of Medicines on the Ocular Surface".

BACKGROUND OF THE INVENTION

1. Field of the Invention

This invention relates broadly to devices used in ophthalmology and optometry. More particularly, this invention relates to devices for the administration of topical medicines to the ocular surface.

2. State of the Art

During the preparation of a patient for ocular surgery, e.g. cataract surgery, the eye is usually treated with medication to anaesthetize the eye. Typically, anaesthesia is injected behind the eye with a needle. However, inserting a needle behind the eye requires a skilled surgeon or anesthesiologist and has inherent dangers. For example, the globe or nerve of the eye may be perforated by the needle resulting in catastrophic vision loss. In addition, because the eye is numb and blinded for several hours, the eye has to be patched post-operatively.

One potential alternative without the dangers of needle administration, and which does not require post-operative patching, is simply to provide topical medicines to the tear film of the eye and have the medication be absorbed into the eye through the tear film. Recently, so called "topical anaesthesia" has become increasingly popular.

However, conventional topical administration of medicines has several drawbacks. First, only a relatively small volume of the total volume of a drop is provided to the tear film. The majority of the drop, as soon as it is applied, either runs down the cheek, or drains and is actively pumped through the naso-lacrimal duct system. Because the drops run or drain away from the eye, multiple applications of drops are required, e.g., every five minutes during the thirty minutes prior to examination or surgery. In addition, multiple drops are required because the tear film is continually replaced with fresh tears from the lacrimal gland and other accessory tear glands. Second, drops intended for the tear film and ocular surface, but which enter the naso-lacrimal duct system can have serious systemic side effects when absorbed through the lacrimal sac and nasopharynx. The multiple application of drops increases undesirable system absorption. Third, the multiple application of drops is an inefficient use of staff labor and causes discomfort to the patient prior to surgery. Fourth, there are economic disadvantages inherent in the inefficient administration of drops; i.e., a substantial volume of each drop running down the patient's cheek, given the high cost of these medicines.

As a result, there has been activity in the field of ocular medicinal and anaesthetic administration to better provide topical medicines to the eye and to provide for their sustained release. For example, and as shown in prior art FIG. 1, which is representative of U.S. Pat. No. 3,618,604 to Ness, an ocular insert 10 is positioned in the fornix 12 of the eye between the sclera 16 and the lower lid 18. The insert 10 has imperforate walls 20 which hold a drug. When the insert is placed into the eye, the drug diffuses through the walls and into the eye. However, the insert is difficult to manufacture, can rupture or leak, and would need to be pre-manufactured with the drug inside the walls (and is therefore not adaptable to releasing a particular dose of medicine, as prescribed by a physician, if the insert is not manufactured with such dosage). In addition, it is difficult to control and obtain desired release rates. Moreover, the amount of medicine that can be held by the insert is limited to the size of an insert which can be held in the fornix of the eye of a patient. Similar devices are disclosed in U.S. Pat. No. 3,916,899 to Theeuwes et al., U.S. Pat. No. 4,014,335 to Arnold, and U.S. Pat. No. 5,378,475 to Smith et al., each suffering from all or several of the drawbacks described above.

Another device for the administration of medicine is the Bloomberg Ophthalmic Ring™ sold by Oasis Medical and Ultracell Medical Technologies, and represented in prior art FIG. 2. The Bloomberg Ophthalmic Ring™ is a ring 30 of absorbent material which can be soaked in a medicine, e.g., an anaesthetic. With respect to anaesthesia, the ring-shaped design concentrates the anaesthesia in the desired locations; i.e., at the deep ciliary nerves and conjunctiva nerves, providing a profound anaesthetic effect. However, the ring does not hold much anaesthetic (or other medicine) and more anaesthetic may be required during surgery. Once the eye has absorbed the medicine from the ring, the ring can be resaturated using a syringe. Therefore, while the Bloomberg Ophthalmic Ring™ does not require replacement after the medicine has diffused out of the ring, as the ring can be resaturated, the ring nevertheless suffers from having a limited initial capacity. In addition, extreme care must be taken while injecting additional anaesthetic into the ring. Moreover, the rate at which medicine diffuses out of the ring is also difficult to control. Further, the ring must be in contact with the eye during ocular surgery, and thus often creates a physical obstacle to the surgeon at the time of surgery.

SUMMARY OF THE INVENTION

It is therefore an object of the invention to provide an ocular drug delivery device which steadily releases medicine to the ocular surface, thus resulting in higher, more consistent levels of drug administration to the eye.

It is another object of the invention to provide an ocular drug delivery device which accurately dispenses a measured amount of medicine to the ocular surface.

It is also an object of the invention to provide an ocular drug delivery device which does not have a predefined or limited capacity.

It is a further object of the invention to provide an ocular drug delivery device which does not require the use of needle.

It is an additional object of the invention to provide an ocular drug delivery device which is easy to use and may be may be utilized by a patient for the self-administration of topical ocular medicines.

It is also an object of the invention to provide an ocular drug delivery device which is easy to manufacture.

In accord with these objects which will be discussed in detail below, an ocular drug delivery device is provided. The device includes a reservoir locatable outside the eye or ocular adnexa (accessory structures of the eye) of a patient during drug delivery, and a conduit having one end coupled to the reservoir and a free end which is positionable within the lower fornix of the eye of a patient.

According to a first embodiment of the invention, the reservoir is preferably made of an absorbent material, e.g, methylcellulose paper, and is also preferably chosen or treated such that the material changes color when wet, thereby indicating that the reservoir contains medicine. The reservoir preferably also has an impermeable backing which acts as a barrier between the medicine and facial skin of the patient, thus reducing systemic absorption. Preferably the backing has raised edges to prevent medicine from rolling off the reservoir surface. The backing is also preferably provided with an adhesive for removably securing the reservoir to the face of the patient, particularly to an area adjacent the eye. The free end of the conduit may be shaped to increase patient comfort or surface area contact with the tear film. Through capillary action, the medicine flows from the reservoir through the conduit and into the eye. As a result, a large reservoir outside the immediate area of the eye is provided for storing medicine, and the rate of delivery of the medicine to the eye may be adjusted according to the size and material of the conduit.

According to a second embodiment of the invention, the reservoir is a hollow container and the conduit is a thin strip of absorbent material preferably encased in a sheath. The reservoir is large enough to hold several milliliters of medicine. The reservoir is provided with an aperture through which medicine is provided to the reservoir. The aperture is preferably sealable with a closure to prevent medicine from leaking or evaporating from the reservoir. A portion of the reservoir is preferably provided with an adhesive to secure the reservoir to the skin of the patient. The device is particularly well suited to patients who require frequent ocular medicinal administration for a relatively long period of time (e.g., corneal ulcer patients), and who would otherwise require periodic interruption of their procedure for medicinal administration.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
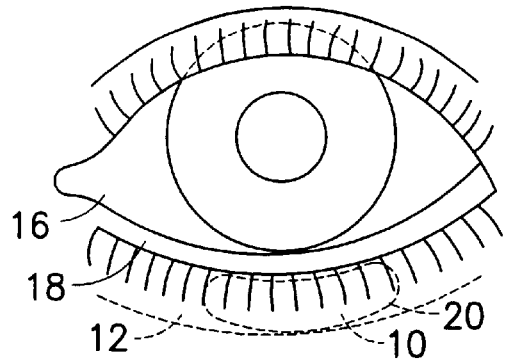
FIG. 1 is a prior art ocular drug delivery device.
Figure 2:
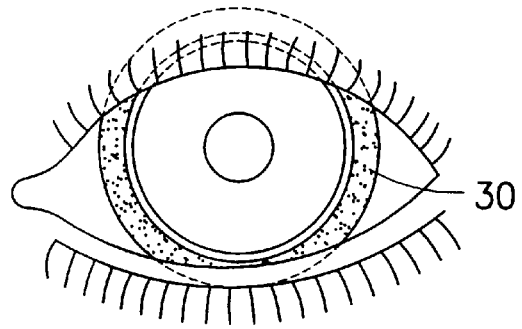
FIG. 2 is another prior art ocular drug delivery device.
Figure 3:
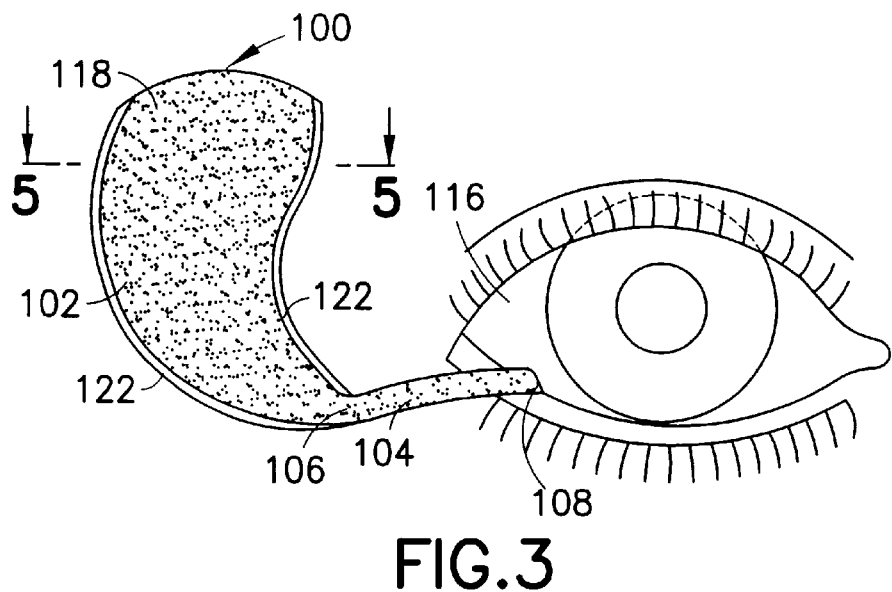
FIG. 3 is an enlarged front view of an ocular drug delivery device according to a first embodiment of the invention adhered to the face of a patient and positioned adjacent to the eye of the patient.
Figure 4:
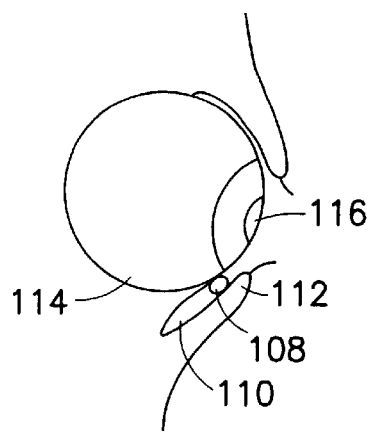
FIG. 4 is a broken side elevation corresponding to FIG. 3.

Turning now to FIGS. 3 and 4, an ocular drug delivery device 100 according to the invention is shown. The device includes a reservoir 102 which stores medicine and a relatively narrow conduit 104 having one end 106 coupled to the reservoir and a free end 108 which is placeable in the lower fornix 110 of an eye 116; i.e., between the lower lid 112 and sclera 114 (FIG. 4). The reservoir 102 provides medicine to the conduit 104 and the conduit provides medicine to the eye 116 of the patient through capillary action.

Figure 5:
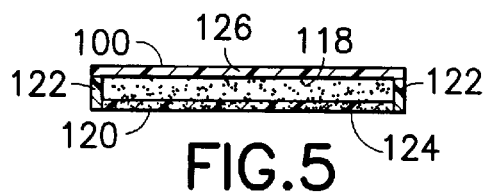
FIG. 5 is a cross-section across line 5—5 of FIG. 3.

The reservoir 102 is made of an absorbent material 118, preferably methylcellulose, e.g., Whatman #10 filter paper, or another cellular material, e.g., materials sold under the trademarks merocel® by Merocel Surgical Products and Ultracell™ by Ultracell Medical Technologies Inc. In addition, the absorbent material is preferably colored in a relatively light or medium hue such that when the material is wet, the material will have a relatively darker appearance. The color of material is thereby able to provide an indication that medicine is contained in the reservoir. Preferably the reservoir 102 is of a size which can hold sufficient medicine for most applications. Indeed, a one and half centimeter square surface area for the absorbent material has been experimentally shown to store four drops of medicine which, if supplied slowly to the eye without loss, is sufficient for most applications. As seen in FIG. 5, the reservoir is provided with a backing 120 made of an impermeable material, e.g., plastic. The backing 120 is preferably provided with an edge 122 surrounding at least a portion of the absorbent material 118 of the reservoir to prevent medicine placed onto the absorbent material from rolling off the reservoir. Preferably an adhesive 124, e.g., a skin adhesive the same as, or of a type similar to, that used for surgical tape and which is available from Baxter International Inc. and 3M Company, is provided on the backing 120 for removably adhering the reservoir 102 to the face of the patient.

A cover 126 may also be provided over all or a portion of the of the absorbent material of the reservoir to inhibit evaporation of the medicine and to prevent environmental contamination of the absorbent material. The cover 126 is preferably a thin, flexible, impermeable film having a hole, slit or other opening through which medicine may be provided to the absorbent material 118.

Figure 6:
FIG. 6 is an enlarged view of the end of the conduit of the first embodiment of the ocular drug delivery device.
Figure 6A:
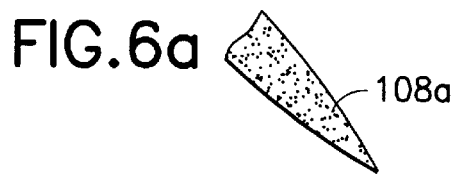
FIG. 6a is an enlarged view of an alternate embodiment of the end of the conduit of the first embodiment of the ocular drug delivery device.
Figure 6B:
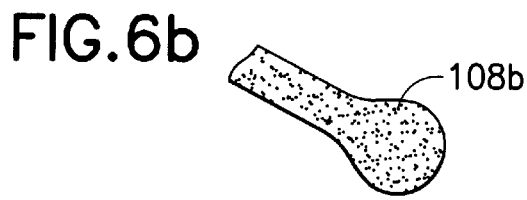
FIG. 6b is an enlarged view of another alternate embodiment of the end of the conduit of the first embodiment of the ocular drug delivery device.

The conduit 104 is also made from a non-toxic, absorbent material and may be made from the same material, or even the same piece of material, as the reservoir 102. The conduit may also be provided with a backing and adhesive (not shown), but preferably any backing or adhesive on the conduit 104 does not extend to the free end 108 of the conduit where the conduit enters the fornix 110. The conduit 104 preferably has a width of 1.5 mm, but sizes from 1 mm to 6 mm have been experimentally shown to provide satisfactory results and other sizes can also be used. The conduit 104 may have a straight free end 108 (FIG. 6), i.e., substantially constant in width over its entire length, a tapering free end 108a (FIG. 6a), or an enlarged free end 108b (FIG. 6b). An enlarged free end 108b provides relatively greater surface area contact with the tear film of the eye and increases the rate of medicinal flow from the reservoir to the eye.

Referring again to FIGS. 3 and 4, in practice, the reservoir 102 of the ocular drug delivery device 100 is removably adhered with the adhesive 124 to the face of the patient, adjacent the eye. A drop of topical anaesthetic is placed into the eye, and the conduit 104 is positioned in the fornix 110 of the eye 116. The drop of topical anaesthetic prevents the conduit from causing discomfort to the eye. Several drops of medicine are then provided to the absorbent material 118 of the reservoir. The impermeable backing 120 prevents the medication from contacting the skin of the patient and the edges 122 of backing around the absorbent material prevent the medication from rolling off or dripping out of the reservoir. Capillary action (and/or gravity if the reservoir is placed above the fornix) causes the medicine to move from the reservoir, through the conduit, and to the eye. The rate at which the medicine moves from the reservoir, through the conduit and into the eye can be chosen by selecting the size (i.e., width or diameter) of the conduit, the shape of the free end of the conduit, and the conduit material. The capacity of the reservoir is limited only by its size, which, since it is located outside the eye, is quite variable. Sustained medicinal release can thereby be provided over a relatively long period of time. In addition, as the reservoir of the device is located on the face of the patient, and not in the fornix of the eye, medicine may easily be added to the reservoir with an eye dropper without disturbing the patient. Moreover, as the medicine is not lost running down the cheek of the patient, less medicine is used. The ocular drug delivery device is suitable for delivery of many medicines, including, but not limited to, anaesthesia, antibiotics, dilation drops, and glaucoma medications.

Experimental testing has confirmed the performance of the ocular drug delivery device of the invention. During an experiment, the right eye of a subject was provided with the ocular drug delivery (i.e., with the reservoir adjacent the right eye and the free end of the conduit tucked in the fornix of the eye), and the left eye had no device coupled thereto. A single drop of tropicamide 1% was applied to the reservoir adjacent the right eye, and also directly to the surface (i.e., the tear film) of the left eye. Next, a single drop of phenylephrine 2.5% was placed on the reservoir and also a single drop of phenylephrine 2.5% was placed onto the surface of the left eye. No more drops were applied thereafter. Within five minutes there was a noticeable dilation in the right eye, yet no discernable change in dilation of the left eye. At twenty minutes, the right eye was fully dilated at about 9 mm and the left eye was partially dilated at about 6 mm. Six hours later the pupil of the right eye was still fully dilated and the pupil of the left eye had returned to normal physiologic size and reactivity.

Figure 7:
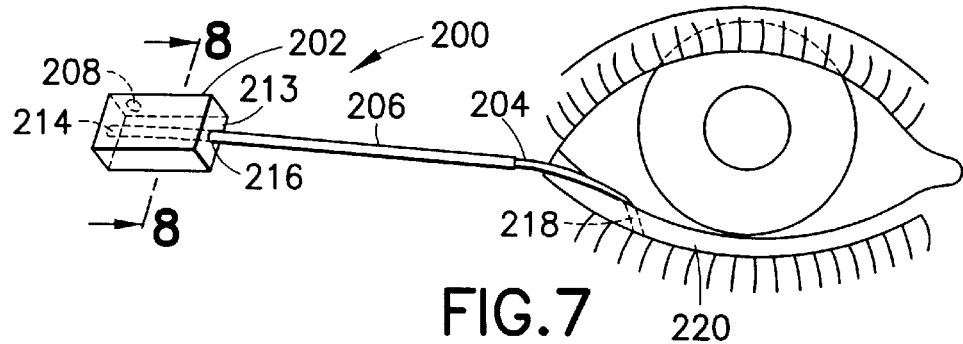
FIG. 7 is a side elevation of an ocular drug delivery device according to a second embodiment of the invention adhered to the face of a patient adjacent the eye of the patient.
Figure 8:
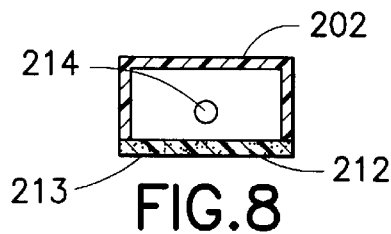
FIG. 8 is a cross-section through line 8—8 of FIG. 7.

Turning now to FIG. 7, a second embodiment of an ocular drug delivery device 200, substantially similar to the first embodiment, is shown. The device generally includes a reservoir 202, a conduit 204 coupled to the reservoir, and preferably a sheath 206 extending over a portion of the conduit 204. The reservoir 202 is made of an impermeable material, e.g., plastic, and is a hollow container able to store ocular medicine. The reservoir as shown is rectangular in shape, but may be any hollow shape. Referring to FIG. 8, the reservoir is preferably provided with an adhesive backing 212 on one side 213 of the reservoir for adhering the reservoir to the face of a patient. The reservoir includes an aperture 208, preferably in an upper portion of the reservoir, through which medicine can be provided to the reservoir.

Figure 9A:
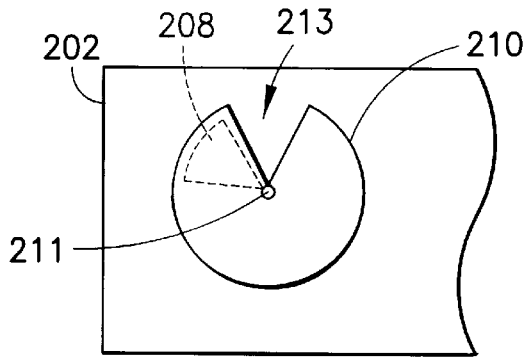
FIGS. 9a and 9b are enlarged broken top views of an openable closure for the reservoir of the ocular drug delivery device of FIG. 7, in closed and open positions, respectively.
Figure 9B:
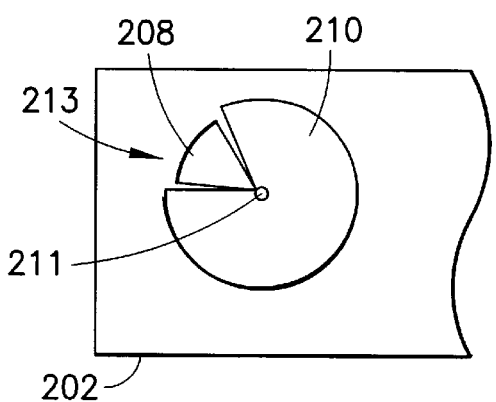

Referring to FIGS. 9a and 9b, a closure 210 is preferably provided over the aperture 208. Preferably the closure 210 is a disc having an open portion 213. The closure 210 is rotatable on an axle 211 relative to the aperture 208 such that the closure 210 can seal the aperture (FIG. 9a) and prevent spillage or evaporation of medicine from the reservoir, or rotated to provide access to the aperture 208 through the open portion 213 (FIG. 9b) enabling the reservoir to be filled and refilled with medicine. The closure 210 can then be rotated to seal the aperture 208.

Figure 10A:
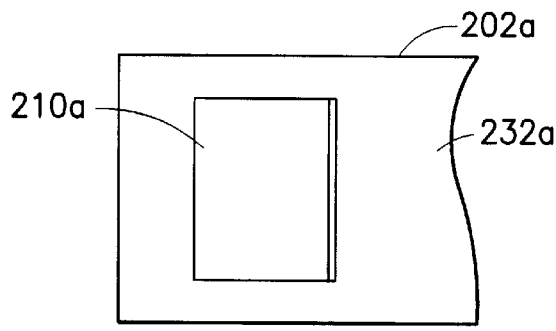
FIG. 10a is a enlarged broken top view of an alternate embodiment of an openable closure for the reservoir of the ocular drug delivery device of FIG. 7, in a closed position.
Figure 10B:
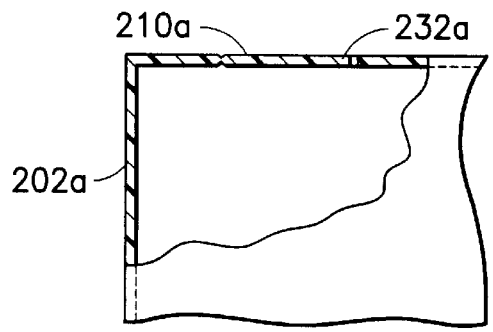
FIG. 10b is a broken side elevation of the openable closure of FIG. 10a, in a closed position.
Figure 10C:
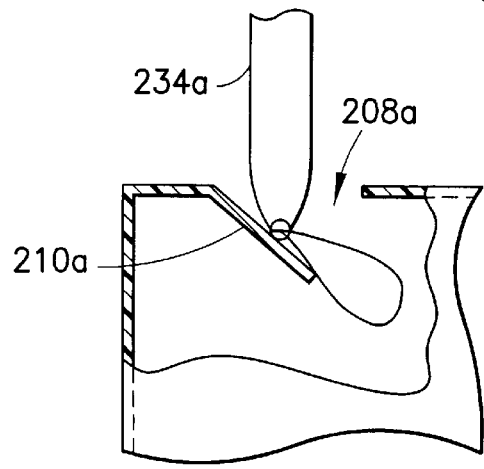
FIG. 10c is a view similar to FIG. 10b of the openable closure in an open position.

Turning now to FIGS. 10a through 10c, an alternate closure 210a is provided for sealing the aperture 208a of the reservoir 202a. The closure 210a is a resilient flange integrally molded with the reservoir 202a and lies substantially coplanar with a side 232a of the reservoir (FIGS. 10a and 10b). An eye dropper 234a or syringe can depress the flange 210a to enter the aperture 208a and release medicinal drops into the reservoir 202a (FIG. 10c). Once the eye dropper 234a is removed from the aperture 208a of the reservoir, the flange 210a bends back to a position substantially coplanar with the side 232a of the reservoir (FIG. 10b).

Referring back to FIGS. 7 and 8, the conduit 204 is made from an absorbent material and includes one end 214 which extends into the reservoir 202 through a hole 216 in the reservoir, and a free end 218 positionable in the fornix 220 of the eye. The sheath 206 is preferably provided over the conduit 204 from the reservoir 202 to a point on the conduit adjacent the free end 218. The sheath 206 is preferably a flexible, plastic capillary tube.

In practice, the reservoir 202 is positioned on the face of the patient by the adhesive backing 212. A drop of topical anaesthetic is placed into the eye, and the conduit 204 is positioned in the fornix 220 of the eye. Several drops of medicine are then provided into the reservoir through the aperture 208. Capillary action and/or gravity causes the medicine to move from the reservoir, through the conduit, and to the eye. The rate at which the medicine moves from the reservoir, through the conduit and into the eye is chosen by selecting the size (i.e., width or diameter) of the conduit, the shape of the free end of the conduit, and the conduit material. A relatively large amount of medicine may be stored in the reservoir, providing sustained release over a relatively long period of time, e.g., twelve hours. This is especially relevant for corneal ulcer patients, who otherwise through conventional topical medicinal administration may be disturbed every half hour or hour for one to three days for the administration of antibiotic drops. Medicine may easily be added to the reservoir through the closure 210 with an eye dropper without disturbing the patient.

There have been described and illustrated herein several embodiments of a ocular drug delivery device and a method of providing medicine to the eye. While particular embodiments of the invention have been described, it is not intended that the invention be limited thereto, as it is intended that the invention be as broad in scope as the art will allow and that the specification be read likewise. Thus, while particular relative sizes of the reservoir, the conduit, and the eye of a patient have been shown in the drawings, it will be understood that the sizes of the reservoir and conduit relative to each other and relative to the eye could be different. In addition, while methylcellulose paper has been disclosed as being a preferred material for the reservoir (in the first embodiment) and the conduit, it will be appreciated that other absorbent materials, e.g., other cellulose materials, saturable (i.e., porous) plastic and nylon meshes, sponges, and cloth, can be used as well. Furthermore, while in the first embodiment the reservoir is illustrated as being generally kidney-shaped, it will be appreciated that the reservoir may be of another shape, e.g., rectangular, triangular, round, or oval. Moreover, while the reservoir of the first embodiment is shown substantially planar, it will be appreciated that the reservoir may be of a more three dimensional shape, e.g., cubic, spherical, or wedge-shaped.

Also, while a cover has been described for use over the reservoir of the first embodiment of the device, it will be appreciated that the cover need not be used. In addition, with respect to the second embodiment, while several closures have been disclosed, it will be appreciated that other closure means may also be provided. Furthermore, while particular configurations materials have been disclosed in reference to the reservoir, the conduit, and the sheath, it will be appreciated that other materials could be used as well. Moreover, while closures having certain shapes and opening operations been disclosed, it will be appreciated that the closures may have other shapes and may operate to open and seal the aperture in another manner. In addition, while it is presumed that capillary action and gravity are primarily responsible for moving the medicine from the reservoir, through the conduit, and to the eye, it will be appreciated that other mechanisms, e.g., the pumping of fluid out of the eye and conduit through the action of the lids, may be partially or primarily responsible for the movement of the medicine. It will therefore be appreciated by those skilled in the art that yet other modifications could be made to the provided invention without deviating from its spirit and scope as so claimed.

What is claimed is:

1. An ocular drug delivery device for delivering a medicine to an eye of a patient, comprising:
   a) a reservoir means for storing the medicine, said reservoir means adapted to be located outside the eye during delivery of the medicine to the eye; and
   b) a conduit means for conveying the medicine from said reservoir means to the eye, said conduit means having a first end coupled to said reservoir means and a second end adapted to be in contact with the eye during delivery of the medicine to the eye.

2. An ocular drug delivery device according to claim 1, wherein:
   said conduit means comprises an absorbent material.

3. An ocular drug delivery device according to claim 2, wherein:
   said absorbent material is selected from a group consisting of methylcellulose, plastic mesh and nylon mesh.

4. An ocular drug delivery device according to claim 2, wherein:
   said conduit means further comprises a flexible sheath extending over said absorbent material.

5. An ocular drug delivery device according to claim 4, wherein:
   said sheath is made of plastic.

6. An ocular drug delivery device according to claim 2, wherein:
   said reservoir means comprises an absorbent material.

7. An ocular drug delivery device according to claim 6, wherein:
   said reservoir means includes an impermeable backing on a side of the absorbent material.

8. An ocular drug delivery device according to claim 7, wherein:
   said impermeable backing includes an adhesive means for removably adhering said reservoir to the face of the patient.

9. An ocular drug delivery device according to claim 8, wherein:
   said reservoir means includes an impermeable cover over substantially the entire surface area of said absorbent material.

10. An ocular drug delivery device according to claim 7, wherein:
    said impermeable backing includes an edge surrounding a portion of said absorbent material.

11. An ocular drug delivery device according to claim 2, wherein:
    said absorbent material comprises color change means for changing the color of said absorbent material when provided with medicine.

12. An ocular drug delivery device according to claim 2, wherein:
    said reservoir means is an impermeable container.

13. An ocular drug delivery device according to claim 12, wherein:
    said reservoir means is provided with an aperture through which medicine is provided to the reservoir.

14. An ocular drug delivery device according to claim 13, wherein:
    said reservoir means is provided with a openable closure means for sealing said aperture and providing access to said aperture.

15. An ocular drug delivery device according to claim 12, wherein:
    said reservoir means is provided with at least one side having an adhesive able to removably couple said reservoir to the face of the patient.

16. An ocular drug delivery device for delivering a medicine to an eye of a patient, comprising:
    a) reservoir means for storing the medicine, said reservoir means adapted to be located outside the eye during delivery of the medicine to the eye;
    b) adhesive means for removably adhering said reservoir means to the face of the patient; and
    c) conduit means for conveying the medicine from said reservoir means to the eye, said conduit means having a first end coupled to said reservoir means and a second end adapted to be in contact with the eye during delivery of the medicine to the eye.

17. An ocular drug delivery device according to claim 16, wherein:
    said reservoir means and said conduit means are made of an absorbent material, and
    said reservoir means is provided with an impermeable backing to which said adhesive means is coupled.

18. A method of delivering a medicine to an eye of a patient, said method comprising:
    a) obtaining a drug delivery device having a reservoir means for storing the medicine and a conduit means for delivering the medicine from the reservoir means to the eye, the conduit means having a first end coupled to the reservoir means and a free end;
    b) placing in the eye the free end of the conduit means and placing external of the eye the reservoir means;
    c) providing the medicine to the reservoir means; and
    d) permitting the medicine to move by capillary action from the reservoir means through the conduit means to the eye.

19. A method according to claim 18, further comprising:
    e) removably coupling the reservoir means to the face of the patient.

20. A method according to claim 18, wherein:
    said step of placing the free end of the conduit includes placing the free end in the fornix of the eye.

* * * * *